(12) United States Patent
Hunaidi et al.

(10) Patent No.: US 7,475,596 B2
(45) Date of Patent: Jan. 13, 2009

(54) NON-DESTRUCTIVE TESTING OF PIPES (75) Inventors: Osama Hunaidi, Ottawa (CA); Marc Bracken, Toronto (CA); Alex Wang, Orleans (CA)

(73) Assignee: National Research Council of Canada, Ottawa, ON (CA)

( * ) Notice: Subject to any disclaimer, the term of this patent is extended or adjusted under 35 U.S.C. 154(b) by 0 days.

(21) Appl. No.: 11/952,582

(22) Filed: Dec. 7, 2007

(65) Prior Publication Data

US 2008/0078247 A1    Apr. 3, 2008

Related U.S. Application Data

(62) Division of application No. 11/156,573, filed on Jun. 21, 2005, now Pat. No. 7,328,618.

(51) Int. Cl.
*G01N 29/00* (2006.01)
(52) U.S. Cl. ............................. 73/592; 73/597; 73/602; 73/622; 73/861.42
(58) Field of Classification Search .................. 73/592, 73/597, 598, 602, 622, 861.42
See application file for complete search history.

(56) References Cited

U.S. PATENT DOCUMENTS

| | | | |
|---|---|---|---|
| 4,056,970 A | 11/1977 | Sollish | |
| 4,930,358 A * | 6/1990 | Motegi et al. | 73/861.28 |
| 5,367,911 A * | 11/1994 | Jewell et al. | 73/861.08 |
| 5,531,099 A * | 7/1996 | Russo | 73/40.5 A |
| 5,708,211 A * | 1/1998 | Jepson et al. | 73/861.04 |
| 5,970,434 A | 10/1999 | Brophy et al. | |
| 6,453,247 B1 | 9/2002 | Hunaidi | |
| 6,561,032 B1 | 5/2003 | Hunaidi | |
| 6,889,562 B2 * | 5/2005 | Gysling et al. | 73/861.42 |
| 7,261,002 B1 * | 8/2007 | Gysling et al. | 73/861.42 |
| 7,328,618 B2 * | 2/2008 | Hunaidi et al. | 73/597 |

OTHER PUBLICATIONS

U.S. Appl. No. 12/025,294, filed Aug. 2008, Perry et al.*
Wavenumber Prediction of Waves in Buried Pipes for Water Leak Detection—Muggleton, Brennan and Pinnington—Journal of Sound and Vibration (2002) 249(5), 939-954.
Fluid Transients In Pipes And Tunnels—Speed of propagation of pressure waves—83046—Engineering Sciences Data Unit 251-259 Regent St. London W1R 7AD.
Fluid Transients—Benjamin Wylie and Victor Streeter—FEB Press, P.O. Box 2431, ann Arbour, Michigan 48106 U.S.A.

(Continued)

*Primary Examiner*—Hezron E. Williams
*Assistant Examiner*—Jacques M. Saint-Surin
(74) *Attorney, Agent, or Firm*—Marks & Clerk; Richard J. Mitchell (57) ABSTRACT

To perform a non-destructive condition assessment of a pipe carrying a fluid, an actual value representative of the propagation velocity of an acoustic disturbance propagating between two longitudinally separated points on the pipe is determined. A corresponding predicted value for the propagation velocity is computed as a function of at least one wall thickness parameter of the pipe by using a theoretical model for the propagation of acoustic waves in the pipe that assumes said pipe has a finite wall thickness with a predetermined circumferential thickness profile. The wall thickness parameter is then computed by matching the actual value with the predicted value, for example, by substituting the actual value in a formula predicting the theoretical value.

11 Claims, 4 Drawing Sheets

OTHER PUBLICATIONS

Kramers-Kronig relationship between ultrasonic attenuation and phase velocity—O'Donnell, Jaynes and Miller—J. Acoust. Soc. Am 69(3) 1981 Acoustical Society of America p. 696-701.

Properties of Ordinary Water-Substance—N. Ernest Dorsey, National Bureau of Standards, Washington, D.C.—Reinhold Publishing Corporation 1940.

The Velocity of Water Hammer Waves—Paper 2—I.S. Pearsall—vol. 180 Pt 3E pp. 12 to 20.

Journal of the Hydraulics Division—Proceedings of the American Society of Civil Engineers—Velocity of A Water Hammer Wave in an Elastic Pipe—A.R. Halliwell.

Water As A Standard In the Measurements Of Speed Of Sound In Liquids—W. Marczak, University of Silesia, Institute of Chemistry, Katowice, Poland, pp. 2776 to 2779.

* cited by examiner

NON-DESTRUCTIVE TESTING OF PIPES

CROSS REFERENCE TO RELATED APPLICATION

This application is a divisional under 35 USC 121 of prior U.S. application Ser. No. 11/156,573, filed Jun. 21, 2005, the contents of which are herein incorporated by reference.

FIELD OF THE INVENTION

This invention relates to the non-destructive condition assessment of pipes, and in particular buried pipes or pipes that are otherwise inaccessible, such as fire sprinkler systems and pipelines in the oil and gas industry.

BACKGROUND OF THE INVENTION

Buried pipes, such as pipes used in municipal water systems, lose metal resulting in a reduction in pipe wall thickness, as a result of internal and external corrosion. Sustained wall thickness loss eventually causes the pipe to fail. Such pipes have to be periodically inspected and evaluated for structural adequacy. Accurate information about pipe wall thickness is needed to determine the structural capacity of pipes. Also, monitoring of pipe metal loss is needed to estimate the remaining service life of pipes, which is an important part of maintenance management systems of large pipe networks (e.g., urban water or gas distribution systems). It is therefore desirable to be able to assess the condition of buried pipes in a non-destructive and non-intrusive way, that is without damaging the pipe and without taking it out of service.

One way of determining pipe wall thickness is to obtain pipe coupons (or samples) and then measure the thickness off-site using thickness calipers. Also, wall thickness can be measured using an ultrasonic gauge at locations where the pipe is naturally exposed or intentionally excavated. Both methods provide only a discrete measurement of wall thickness. An alternative method for obtaining a continuous measurement of pipe wall thickness employs ultrasonic or magnetic flux leakage or remote-field eddy current devises which are launched inside pipes using robots (known as pipeline pigs).

Excavating pipes for the purpose of measuring wall thickness is costly, as it requires excavating the pipe at several locations. Also, thickness values based on the coupons may not be statistically representative of the overall condition of the pipe unless a very large number of locations are excavated. Pipeline pigging requires taking the pipe out of service. It is strictly suitable for large diameter pipes with simple geometry (i.e., no abrupt bends). Data acquisition and analysis is very intensive and expensive. The method is used mostly for oil and gas transmission pipelines. It is not suitable for water distribution systems, which are geometrically complex and extensive networks comprised of small-diameter pipes that are usually filled with debris and have no pig launching stations.

SUMMARY OF THE INVENTION

In accordance with the invention, the pipe wall thickness is determined from the average propagation velocity of low-frequency acoustic disturbances in the pipe (e.g., pressure fluctuations). Low-frequencies typically have a value of less than about 1000 Hz. The propagation velocity depends on the internal diameter and circumferential thickness profile of the pipe, density and bulk modulus of elasticity of the fluid, and Young's modulus of elasticity and Poisson's ratio of the pipe wall material. The velocity can be calculated using equations derived theoretically. In the proposed method, the pipe wall thickness is back calculated from these equations using the measured value of the propagation velocity and the above pipe and fluid parameters, which are usually known or easily found.

According to the present invention there is provided a method for the non-destructive condition assessment of a pipe carrying a fluid, comprising detecting an acoustic disturbance propagating past two longitudinally separated points on said pipe; determining an actual value representative of the propagation velocity of said acoustic disturbance; computing a corresponding predicted value for the propagation velocity as a function of at least one wall thickness parameter of said pipe by using a theoretical model for the propagation of acoustic waves in said pipe that assumes said pipe has a finite wall thickness with a predetermined circumferential thickness profile; and computing said wall thickness parameter by matching said actual value with said predicted value.

The acoustic disturbance can propagate in the in-bracket mode, where the source of the disturbance lies between the two points and the disturbance propagates in opposite directions from the source to the separated points, or in the out-of-bracket mode, where the acoustic source lies outside the two points, and the disturbance propagates from the source and sequentially past the two points in the same direction.

The propagation velocity, usually the average propagation velocity, can be determined on-site non-destructively and non-intrusively by measuring the time delay between acoustic signals measured at two points on the pipe that are a known distance apart (e.g., control valves or fire hydrants). Ambient noise in the pipe can be used as the acoustic source.

Alternatively, acoustic noise created by releasing pressurized fluid or by a specially designed device at an in-bracket or out-of-bracket point (e.g., a fire hydrant in the case of water distribution pipes) acoustic noise can be used. Acoustic signals can be measured using a pair of vibration sensors (e.g., accelerometers) or hydrophones. The time delay between the two measured signals is determined using the well-known time-of-flight method or the cross-correlation function (traditional or enhanced) calculated in the time or frequency domains as described in U.S. Pat. No. 6,453,247, the contents of which are herein incorporated by reference. The average propagation velocity in the pipe can then be calculated by dividing the difference between the distances of the sensors from the acoustic source by the time delay.

In addition to determining the average thickness, the acoustic damping capacity of the pipe material can also be determined based on the attenuation of the acoustic signals described above. Alternatively, the damping capacity can be determined based on the width of the frequency spectrum peak that corresponds to the fundamental ring frequency of the pipe or based the logarithmic decrement of transient ring vibration. The frequency spectrum and logarithmic decrement can be found using a simple mechanical impact test at a location where the pipe is exposed, e.g., in an access manhole. The damping capacity of the pipe material can be used to obtain information about its tensile strength, especially for cast iron pipes, based on published relationships. This is helpful in view of the fact that the tensile strength of cast iron pipes varies widely, depending on their source of supply and vintage. For cast iron pipes, the damping capacity increases as their strength decreases, which depends on the carbon content and cooling rate. Carbon content and cooling rate affect the matrix and graphite structure of cast iron and in turn its stress-strain non-linearity. Non-linearity in the form of a hysteresis loop leads to high damping capacity.

The method in accordance with the invention has the advantage of being non-destructive and non-intrusive. All required measurements can be made from the ground surface. The length of the pipe section represented by the average profile can be arbitrarily chosen. Initially, a 100 metres long section, which is the usual distance between fire hydrants in urban areas, can be chosen. Subsequently, if higher resolution is needed, small access holes to the pipe may be drilled, e.g., using keyhole vacuum excavation technologies, to measure the thickness over shorter pipe sections. Alternatively, arrays of closely spaced hydrophones may be inserted into pipes through fire hydrants or corporation stops. The measurement and calculation of the pipe wall thickness can be easily made using Windows-based PC software. The proposed method is easy to implement (e.g., in conjunction with routine leak detection surveys). Also, it does not require a high level of operator skill.

BRIEF DESCRIPTION OF THE DRAWINGS

The invention will now be described in more detail, by way of example only, with reference to the accompanying drawings, in which.

DETAILED DESCRIPTION OF THE PREFERRED EMBODIMENTS

In order to assist in understanding the invention, it is helpful to consider the underlying theory.

The propagation velocity of acoustic waves in an unbounded fluid body is defined by the following equation:

$$v_o = \sqrt{\gamma K/\rho} \quad (1)$$

where K is the bulk modulus of elasticity of the fluid, $\rho$ is its density, and $\gamma$ is the ratio of the specific heats of the fluid (i.e., the ratio of the fluid's heat capacity in a constant pressure process to the heat capacity in a constant volume process).

The derivation of this equation can be found in Pearsall, I. S. "The velocity of water hammer waves", Proceedings of the Institution of Mechanical Engineers, Vol. 180, Part 3E, pp. 12-20, 1965, the contents of which are herein incorporated by reference.

For a nearly incompressible liquid, which is the case under normal temperatures and pressures in water distribution pipes, $\gamma$ is approximately equal to unity. Then, Eq. (1) becomes:

$$v_o = \sqrt{K/\rho} \quad (2)$$

The elasticity of the wall of a pressurized fluid-carrying pipe reduces the velocity of acoustic waves in the fluid. The amount of the reduction of the velocity depends on the size and shape of the cross-sectional area of the pipe and the elastic modulus of the material of the pipe. The general equation of the velocity of acoustic waves in the fluid is defined by the following equation:

$$v = v_o \Big/ \sqrt{1 + \gamma K\left(\frac{1}{A}\frac{\partial A}{\partial p}\right)} \quad (3)$$

where A is the cross-sectional area occupied by the fluid, p is pressure inside the pipe, and $v_o$ is defined by Eq. (1). For a nearly incompressible liquid, $\gamma$ is approximately equal to unity. This equation is explained in Wylie, E. B., and Streeter, V. L. *Fluid Transients*, McGraw-Hill, New York, 1982. the contents of which are herein incorporated by reference.

For such fluids, Eq. (3) becomes:

$$v = v_o \Big/ \sqrt{1 + K\left(\frac{1}{A}\frac{\partial A}{\partial p}\right)} \quad (4)$$

where $v_o$ is defined by Eq. (2).

For accurate estimation of the velocity, it is necessary to consider the variation of K and $\rho$ with the temperature, air content, and pressure of the fluid. For pipes having very thick walls or for gas-filled pipes, $$\frac{\partial A}{\partial p}$$

is negligible and therefore $v \approx v_o$. On the other hand, for very flexible pipes, the acoustic velocity may be approximated as:

$$v = \sqrt{\frac{A}{\rho}\frac{\partial p}{\partial A}} \quad (5)$$

The cross-sectional area strain of the pipe, $\partial A/A$, is caused by the change in total circumferential strain, $\partial \epsilon_\theta$, which in turn is caused by the change in pressure, $\partial p$. The total circumferential strain is equal to:

$$\partial \epsilon_\theta = \frac{\partial \sigma_\theta - \mu \partial \sigma_l}{E} \quad (6)$$

where $\sigma_\theta$ and $\sigma_l$ are circumferential and axial stresses in the pipe wall, respectively, and E and $\mu$ is the elastic modulus and Poisson's ratio of the pipe material.

For a circular pipe, and considering a small angular part of the cross-sectional area defined by the angle $\partial \theta$, the partial change in the area is:

$$\partial A^\theta = (R\partial\theta)\partial u_R \quad (7)$$

where R is the internal radius of the pipe and $\partial u_R$ is the change in the radial displacement at radius R. Dividing Eq. (7) by $(A\partial p)$ and integrating over $\theta$ leads to:

$$\frac{1}{A}\frac{\partial A}{\partial p} = \frac{1}{\pi R \partial p}\int_0^{2\pi} \partial u_R d\theta \quad (8)$$

where the change in the radial displacement at radius R, $\partial u_R$, is equal to:

$$\partial u_R = \frac{R\partial\theta + \partial\varepsilon_\theta^T R\partial\theta}{\partial\theta} - R \quad (9)$$

$$= \partial\varepsilon_\theta^T R$$

For a pipe that is thin-walled, that is where the ratio between its diameter and thickness is large, stresses in the pipe wall are nearly uniform across its thickness. Consideration of the equilibrium of forces acting on half of the cross-sectional area of the pipe wall shows the circumferential stress to be:

$$\sigma_\theta = \frac{Rp}{t} \text{ and } \partial\sigma_\theta = \frac{R\partial p}{t} \quad (10)$$

where t is the thickness of the pipe wall defined by:

$$t = f(\theta) \quad (11)$$

For a pipe that's free to move axially, e.g., with expansion joints throughout its length, or for a pipe material having a high modulus of elasticity, e.g., steel or concrete, the change in axial stress, $\partial\sigma_l$, is negligible and can be assumed to be zero. For other fixation conditions, the change in the axial stress can be significant and should be taken into account. For example, for a pipe constrained against axial movement throughout its length, $$\epsilon_l = 0$$

and:

$$\partial\sigma_l = \mu\partial\sigma_\theta \quad (12)$$

Substituting Eq. (10) and (12) in (6), Eq. (6) in (9), and finally Eq. (9) in (8) leads to (assuming that the wall thickness profile is symmetric about the pipe's centreline):

$$\frac{1}{A}\frac{\partial A}{\partial p} = c\frac{r}{\pi E}\int_0^{2\pi}\frac{d\theta}{f(\theta)} \quad (13)$$

$$= c\frac{D}{\pi E}\int_0^\pi \frac{d\theta}{f(\theta)}$$

where D is the diameter of the pipe and c is a factor that takes into account the fixation method of the pipe and is given by:

$$c = \begin{cases} 1 & \text{for a pipe having expansion joints throughout its length or having a high modulus of elasticity} \\ 1-\mu^2 & \text{for a pipe constrained against axial movement throughout its length} \end{cases} \quad (14)$$

Pipes buried in corrosive soils may not loose their thickness evenly around the circumference. Most likely, this is due to the formation of corrosion cells on the outer surface of the pipe as a result of differential aeration. This happens when the pipe's cross-section is partially in contact with two soils, for example, a porous and hence well-aerated soil, such as soils used for backfill, and an impermeable and hence poorly aerated soil, such as native clay soils. Differential aeration may also occur on the internal surface of the pipe due to the accumulation of deposits at the bottom of the pipe. To take this phenomenon into account, the wall thickness of the pipe may be assumed to vary linearly with the angular coordinate as follows:

$$t = \begin{cases} \frac{t_{max} - t_{min}}{\pi}\theta + t_{min} & \text{for } -f\pi \leq \theta \leq f\pi \\ t_{max} & \text{for } f\pi \leq \theta \leq -f\pi \end{cases} \quad (15)$$

where f is the fraction of the pipe cross-section having non-uniform thickness, and $t_{min}$ is the minimum wall thickness at $\theta=0$ and $t_{max}$ is the maximum wall thickness at $\theta=\pi$. The mean thickness, $t_{mean}$, is then equal to:

$$t_{mean} = f\frac{t_{max} + t_{min}}{2} + (1-f)t_{max} \quad (16)$$

A linear circumferential thickness profile was selected in the example above for its simplicity and ease of demonstration. However, if more accurate results are required, more representative profiles can be used. Substituting Eq. (15) in (13) and evaluating the integral leads to:

$$\frac{1}{A}\frac{\partial A}{\partial p} = c\frac{D}{E}\left[\frac{(1-f)}{t_{max}} + \frac{\ln[ft_{max} + (1-f)t_{min}] - \ln(t_{min})}{t_{max} - t_{min}}\right] \quad (17)$$

and substituting Eq. (16) in (4) leads to the following equation for the pipe's acoustic velocity:

$$v = v_o \bigg/ \sqrt{1 + cD\frac{K}{E}\left[\frac{(1-f)}{t_{max}} + \frac{\ln[ft_{max} + (1-f)t_{min}] - \ln(t_{min})}{t_{max} - t_{min}}\right]} \quad (18)$$

where c is defined by Eq. (14).

The validity of Eq. (18) can be checked by considering the special case of a pipe having uniform thickness profile, i.e., $t_{min} = t_{max} = t$. Since $$\lim_{a\to 0}\frac{\ln(x) - \ln(x-a)}{x - (x-a)} = \frac{1}{x} \quad (19)$$

Eq. (18) becomes:

$$v = v_o \bigg/ \sqrt{1 + c\frac{D}{t}\frac{K}{E}} \quad (20)$$

The velocity of acoustic waves given by Eq. (20) is the same as that derived in standard textbooks for fluid-filled cylindrical thin-walled pipes with a uniform cross-section.

The errors resulting from assumption that the pipe is thin-walled, as is the case in U.S. Pat. No. 6,531,032, are small for the purpose of locating pipe leaks. However, for thickness measurements, the error may not be sufficiently small. For example, for a 152 mm cast iron pipe that is 10 mm thick with v=1218 m/s, the back-calculated uniform thickness is equal to 9 mm, assuming that the pipe is thin-walled. This corresponds to a spurious loss of 10%. For more accuracy, full account must be taken of the variation of stresses across the thickness of the pipe wall.

The radial displacement at the inner radius for an unconstrained pipe with expansion joints throughout its length, taking into account the variation of stresses across its thickness, is given by:

$$\partial u_R \frac{\partial p}{E}\left[\frac{D^3}{4t(D+t)} + \frac{D}{2}(1+\mu)\right] \quad (21)$$

and for pipes with constrained axial movement throughout it's given by:

$$\partial u_R \frac{\partial p}{E}\left[\frac{D^3}{4t(D+t)}(1+\mu^2) + \frac{D}{2}(1+\mu)\right] \quad (22)$$

Halliwell, A. R. "Velocity of a water hammer wave in an elastic pipe", Proceedings of the American Society of Civil Engineers, Journal of the Hydraulics Division, Vol. 89, No. HY4, pp. 1-20, 1963.

Substituting Eq. (15) in (21) and (22), Eq. (21) and (22) in (8), Eq. (8) in (4) and evaluating the integral leads to the following velocity equation for a pipe with expansion joints throughout its length:

$$v = v_o \bigg/ \sqrt{1 + \frac{K}{E}\left[\frac{D^2}{\pi}F + 2(1+\mu)\right]} \quad (23a)$$

and the following equation for pipes with constrained axial movement throughout its length:

$$v = v_o \bigg/ \sqrt{1 + \frac{K}{E}\left[\frac{D^2}{\pi}F(1+\mu^2) + 2(1+\mu)\right]} \quad (23b)$$

where $$F = \frac{(1-f)\pi}{t_{max}(D+t_{max})} + \frac{1}{\sqrt{b^2-4ac}}\left[\ln\left(\frac{2\pi fa+b-\sqrt{b^2-4ac}}{2\pi fa+b+\sqrt{b^2-4ac}}\right) - \ln\left(\frac{b-\sqrt{b^2-4ac}}{b+\sqrt{b^2-4ac}}\right)\right] \quad (24)$$

$$a = \left(\frac{t_{max}-t_{min}}{\pi}\right)^2 \quad (25a)$$

$$b = \left(\frac{t_{max}-t_{min}}{\pi}\right)(2t_{min}+D) \quad (25b)$$

$$c = t_{min}^2 + t_{min}D \quad (25c)$$

For a thick-walled pipe having a uniform thickness, Eq. (23) becomes:

$$v = v_o \bigg/ \sqrt{1 + \frac{D}{t}\frac{K}{E}\left(\frac{2t}{D}(1+\mu) + \frac{D}{D+t}\right)} \quad (26a)$$

for a pipe with expansion joints throughout its length, and $$v = v_o \bigg/ \sqrt{1 + \frac{D}{t}\frac{K}{E}\left(\frac{2t}{D}(1+\mu) + \frac{D}{D+t}(1-\mu^2)\right)} \quad (26b)$$

for a pipe with constrained axial movement, which are in agreement with expressions derived in standard textbooks for fluid-filled cylindrical thick-walled pipes with a uniform cross-section.

The above formulations for thin and thick-walled pipes with non-uniform circumferential thickness profiles do not take into account shear stresses in the pipe wall that are expected to develop as a result of having unaxisymmetric radial displacement. In the formulation for thin-walled pipes, it is assumed that the cross-section of the pipe remains circular in order to simplify the calculation of the circumferential stress, i.e., Eq. (10). Similarly, to simplify the formulation for thick-walled pipes, radial displacements for pipes with uniform thickness profiles are used. A rigorous formulation, taking into account shear stresses in the pipe wall, is possible. However, such formulation would be too complex and the small gain in accuracy is unwarranted.

The above formulations for both thin and thick-walled pipes do not take into account the inertia of the pipe wall and the surrounding soil. It is assumed that the pipe responds statically to propagating dynamic pressure waves. At low frequencies, well below the ring frequency of the pipe, errors caused by this assumption are small as the pipe's response is dominated by the stiffness of its wall. For example, considering only the inertia of the pipe wall, the velocity equation for a pipe having uniform cross-section and with expansion joints throughout its length, the velocity equation is given by:

$$v = v_o \bigg/ \sqrt{1 + \frac{D}{t}\frac{K}{E}\left(\frac{1}{1-D^2\omega^2\rho_{pipe}/4E}\right)} \quad (27)$$

where $\omega$ is the frequency of the propagating pressure wave (in radians per second) and $\rho_{pipe}$ is the density of the pipe wall material. The derivation of this expressions is explained in Muggleton, J. M, Brennan, M. J., and Pinnington, R. J. "Wavenumber prediction of waves in buried pipes for water leak detection", Journal of Sound and Vibration, Vol. 249, No. 5, pp. 939-954, 2002, the contents of which are herein incorporated by reference.

For the case of a cast iron pipe that is 152 mm in diameter and 12 mm thick, the maximum frequency of acoustic noise signals is typically 800 Hz. The maximum error in velocity resulting from ignoring the inertia of the pipe wall is a miniscule 0.07% (E=128 GPa, $\rho_{pipe}$=7100 kg/m$^3$, K=2.157 GPa at 16° C.). This is also the case for other metallic pipes.

Change in the nominal internal diameter, due to wall thickness loss, is not taken into account. However, such changes can be easily incorporated, although the small gain in accuracy makes the additional effort unwarranted.

In deriving the general form of the velocity equation, i.e., Eq. (3), based on conservation of mass in an infinitesimal pipe section, small terms are neglected. It is assumed that this has a negligible effect on the acoustic velocity. Even if the effect is not so, determination of the bulk modulus of elasticity of the fluid carried by the pipe as described later amounts to calibrating the whole thickness measurement method. The back calculated bulk modulus implicitly includes corrections for approximations made in the derivation of the velocity equation, e.g., neglecting small terms and inertial effects.

The minimum thickness of the pipe, $t_{min}$, can be back calculated using Eqs. (18) or (23) for pipes with linearly varying wall thickness. The maximum thickness, $t_{max}$, is assumed to be equal to the original thickness of the pipe wall, which is usually known or can be measured using a single pipe sample. This is justified based on the observation that a certain part of the pipe's cross-section normally retains its original thickness. This part corresponds to the cathode of the corrosion cell created by differential aeration of the pipe's surface. The minimum thickness can also be calculated using Eq. (16) from the mean thickness back calculated using Eqs. (20) or (26) for pipes having uniform wall thickness. This will lead to less accurate results than would be obtained using Eq. (23) for a thick-walled pipe with linearly varying wall thickness. For the same fixation condition, using Eqs. (18), (20), or (26) underestimates $t_{min}$. If the pipe can be assumed to have a uniform thickness profile (as may be found from experience for a particular area), the average thickness can be back calculated using Eq. 26.

The velocity of acoustic waves in the pipe, v, can be measured by correlating acoustic noise signals, which can be ambient or created intentionally by an acoustic source at a known location. The internal diameter of the pipe, D, bulk modulus of elasticity of the fluid, K, and its density, $\rho$, elastic modulus of the pipe material, E, and its Poisson's ratio, $\mu$, are usually known or can be easily found.

In order to practice the method in accordance with the invention, it is necessary to know the velocity of sound in unbounded fluid, $v_0$ or the bulk modulus of the fluid, and its density. Considering the case of water distribution pipes, the velocity of sound in an unconfined body of pure water is given by:

$$v_o=1.402385\times10^3+5.038813$$
$$T5.799136\times10^{-2}T^2+3.287156\times10^{-4}T^3-1.398845\times10^{-6}T^4+2.787860\times10^{-9}T^5 \qquad (28)$$

where T is the water temperature in ° C. This expression is based on Marczak, W. (1997), Water as a standard in the measurement of the speed of sound in liquids. Journal of the Acoustical Society of America, Vol. 102, No. 5, pp. 2776-2779, the contents of which are incorporated herein by reference.

Table 1 lists the velocity of sound, density and the corresponding bulk modulus of elasticity for temperatures between 0 and 40° C. Density values are based on the *Handbook of Chemistry and Physics*, CRC Press, 85th edition, 2004-2005, the contents of which are incorporated herein by reference. Bulk modulus values were obtained by using Eq. (2).

TABLE 1

Velocity of sound, density and bulk modulus of elasticity of water

| Temperature (° C.) | Velocity of sound (m/s) | Density of water (kg/m$^3$) | Bulk modulus (GPa) |
|---|---|---|---|
| 0 | 1402 | 999.8426 | 1.966 |
| 1 | 1407 | 999.9015 | 1.980 |
| 2 | 1412 | 999.9429 | 1.994 |
| 3 | 1417 | 999.9672 | 2.008 |
| 4 | 1422 | 999.975 | 2.021 |
| 5 | 1426 | 999.9668 | 2.034 |
| 6 | 1431 | 999.943 | 2.046 |
| 7 | 1435 | 999.9043 | 2.059 |
| 8 | 1439 | 999.8509 | 2.071 |
| 9 | 1443 | 999.7834 | 2.083 |
| 10 | 1447 | 999.7021 | 2.094 |
| 11 | 1451 | 999.6074 | 2.105 |
| 12 | 1455 | 999.4996 | 2.116 |
| 13 | 1459 | 999.3792 | 2.127 |
| 14 | 1462 | 999.2464 | 2.137 |
| 15 | 1466 | 999.1016 | 2.147 |
| 16 | 1469 | 998.945 | 2.157 |
| 17 | 1473 | 998.7769 | 2.166 |
| 18 | 1476 | 998.5976 | 2.176 |
| 19 | 1479 | 998.4073 | 2.185 |
| 20 | 1482 | 998.2063 | 2.194 |
| 21 | 1485 | 997.9948 | 2.202 |
| 22 | 1488 | 997.773 | 2.210 |
| 23 | 1491 | 997.5412 | 2.218 |
| 24 | 1494 | 997.2994 | 2.226 |
| 25 | 1497 | 997.048 | 2.234 |
| 26 | 1499 | 996.787 | 2.241 |
| 27 | 1502 | 996.5166 | 2.248 |
| 28 | 1504 | 996.2371 | 2.255 |
| 29 | 1507 | 995.9486 | 2.261 |
| 30 | 1509 | 995.6511 | 2.268 |
| 31 | 1511 | 995.345 | 2.274 |
| 32 | 1514 | 995.0302 | 2.280 |
| 33 | 1516 | 994.7071 | 2.285 |
| 34 | 1518 | 994.3756 | 2.291 |
| 35 | 1520 | 994.0359 | 2.296 |
| 36 | 1522 | 993.6883 | 2.301 |
| 37 | 1524 | 993.3328 | 2.306 |
| 38 | 1525 | 992.9695 | 2.311 |
| 39 | 1527 | 992.5987 | 2.315 |
| 40 | 1529 | 992.2204 | 2.319 |

Limited available information about the compressibility of lake waters indicates that it is not significantly different from that of pure water, see for example Dorsey, N. E. (1940). *Properties of Ordinary Water-Substance*. Reinhold Publishing Corporation, New York, U.S.A. However, the velocity of sound given by Eq. (28) is based on experimental results that have been obtained for pure water at MHz frequencies. Therefore, this equation may not be applicable for pure or ordinary water at frequencies below 1000 Hz, which dominate acoustic signals in water distribution pipes. It was shown by O'Donnell M., Jaynes E. T., and Miller J. G. (1981), Kramers-Kronig relationship between ultrasonic attenuation and phase velocity, J. Acoust. Soc. Am. Vol 69, No 3, pp 696-701 that a system that exhibits attenuation, which is the case for water, must exhibit dispersion, i.e., dependence of phase velocity on frequency. Also, they showed that acoustic velocities at low frequencies are typically lower than those at higher ones. Consequently, the bulk moduli of water in distribution pipes may be lower than those listed in Table 1.

Figure 3:
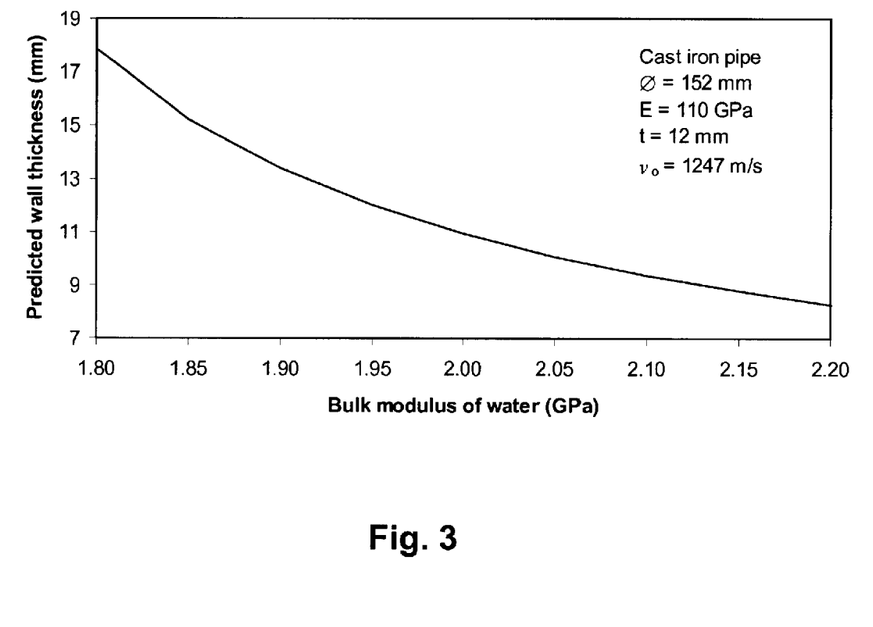
FIG. 3 shows the variation of predicted pipe thickness as a function of bulk modulus of water.

Bulk moduli used for water hammer analysis in some texts and handbooks are the same as those listed in Table 1; while they are slightly lower in others. Small discrepancies in the bulk modulus have a minor effect on water hammer calculations. However, when bulk moduli listed in Table 1 were used with the proposed non-destructive testing method, the predicted thickness loss was overestimated. The dependence of predicted wall thickness on the bulk modulus of water is shown in FIG. 3 for a 12 mm thick, 152 mm Ø pit cast iron pipe having an acoustic velocity of 1247 m/s. For example, using a bulk modulus equal to 2.2 GPa, as used by some texts at 20° C., predicted thickness would be 8.3 mm, while it would be 10.4 mm using a modulus of 2.03 GPa, as used by other texts at 20° C.

The uncertainty regarding the appropriate value of the bulk modulus to be used for thickness calculations can be minimized in accordance with an embodiment of the invention by careful measurement. First, the acoustic velocity is measured for a "reference" pipe of a known wall thickness, diameter and Young's modulus. Preferably, a recently installed pipe of a known class should be used and its Young's modulus should be measured dynamically for an exhumed or leftover sample. Then, the bulk modulus is back calculated from the appropriate theoretical acoustic velocity equation or a numerical model for water-filled pipes together with other already known or measured pipe parameters. Measurement of the acoustic velocity of the reference pipe and other pipes should be performed within few days of each other. This is to ensure that temperatures of the fluids in the pipes are similar.

Alternatively, the bulk modulus may be determined from a relationship established from a set of measurements of the fluid's bulk modulus and temperature for the reference pipe at different times of the year. Determination of the bulk modulus as described here amounts to calibrating the whole thickness measurement method. The back calculated modulus implicitly includes corrections for approximations made in the derivation of the velocity equation, e.g., neglecting small terms and inertial effects.

Following is an example of the determination of the relationship between the bulk modulus of elasticity of the fluid and its temperature. Acoustic velocity was measured for a recently installed 152 mm Ø Class 52 cement-lined ductile iron water distribution pipe having the following temperatures: 20.8, 11.7, and 5.3° C.

For a cement-lined pipe of circular cross-section, the acoustic wave velocity can determined by the following equation, given in Fluid Transients in Pipes and Tunnels: Speed of Propagation of Pressure Waves. Engineering Sciences Data Item No. 83046, ESDU International, 1983, London, U.K:

$$v = \sqrt{\frac{K_w/\rho_w}{1 + K_w \left( \frac{(D-e_p)(1-\mu^2)[(D^2+e_p^2)(1-\mu)+2\mu De_p]}{E_p De_p(D-e_p)(1-\mu) + E_l e_l[(D^2+e_p^2)(1-\mu)+2\mu De_p]} \right)}} \quad (29)$$

where $v$ is velocity of acoustic waves in the pipe, $K_w$ and $\rho_w$ are bulk modulus of elasticity and density of water, respectively; $E_p$, $D$, and $e_p$ are Young's modulus, internal diameter, and metal thickness of the pipe, respectively; $E_l$ and $e_l$ are Young's modulus and thickness of the cement lining, respectively; and $\mu$ is Poisson's ratio, assumed to be the same for ductile iron and the cement lining.

Figure 4:
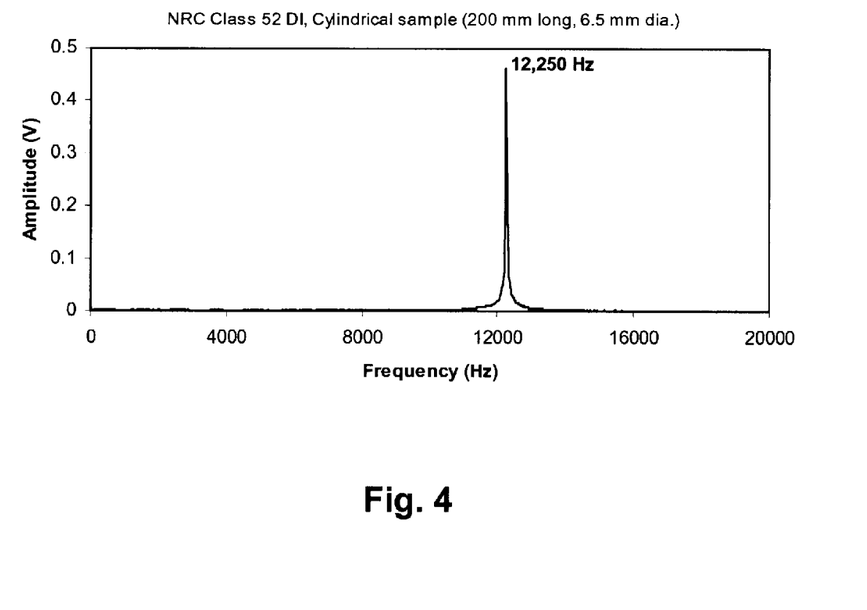
FIG. 4 shows the frequency spectrum of an impact-echo test of a rod sample of an equivalent ductile pipe.

The thicknesses of the metal section and cement lining for 152 mm Ø Class 52 ductile iron pipes are 7.9 and 2 mm, respectively. The thickness of an "equivalent" ductile iron pipe with no cement lining is equal to 8.2 mm, as found from Eq. (29). The equivalent pipe has the same acoustic wave velocity as the cement-lined one. Young's modulus of ductile iron is equal to 169 GPa, as found from the resonance frequency of a rod sample using an impact-echo test that can be seen in FIG. 4; Poisson's ratio was taken equal to 0.3; and Young's modulus of the cement lining was taken equal to 24 GPa. The impact-echo test and modulus calculation was performed in accordance with ASTM standard E 1876-01: Standard test method for dynamic Young's modulus, shear modulus, and Poisson's ratio by impulse excitation of vibration, 2001.

Figure 5:
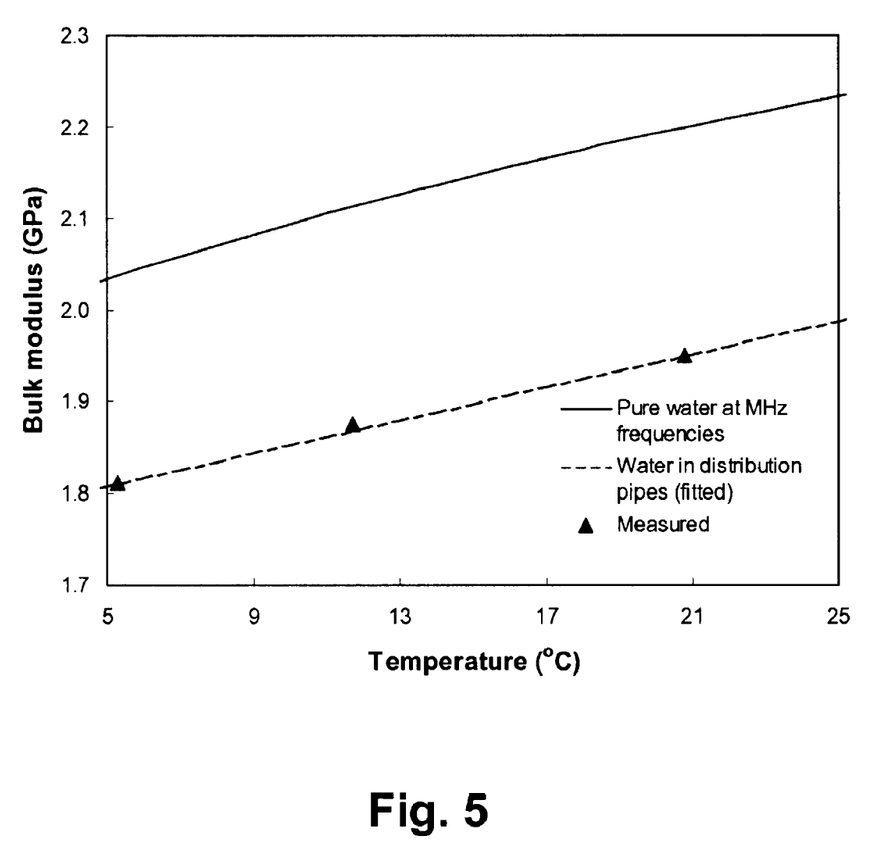
FIG. 5 shows the variation of bulk modulus as a function of temperature for water in distribution pipes at low frequencies and pure water at MHz frequencies.

The bulk modulus of water was back calculated by adjusting its value until the predicted pipe wall thickness was equal to 8.2±0.1 mm. The modulus was found to be 1.95 GPa at 20.8° C., 1.875 GPa at 11.7° C., and 1.81 GPa at 5.3° C. A straight line was fitted to the backcalculated moduli and is shown in FIG. 5 together with moduli based on the velocity of sound given by Eq. (28) for pure water at MHz frequencies. Over the 5 to 25° C. temperature range shown in FIG. 5, which is expected for water in distribution pipes, the modulus for pure water at high MHz frequencies almost varies linearly with temperature. This lends support to the adequacy of the fitted straight line for estimating the bulk modulus of water in distribution pipes.

Figure 1A:
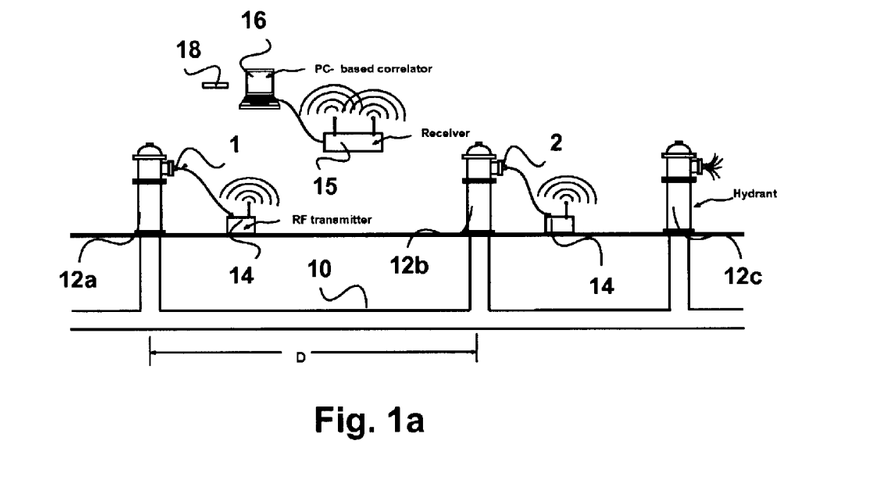
FIG. 1a shows an arrangement for measuring propagation velocity of buried pipes in accordance with a first embodiment.
Figure 1B:
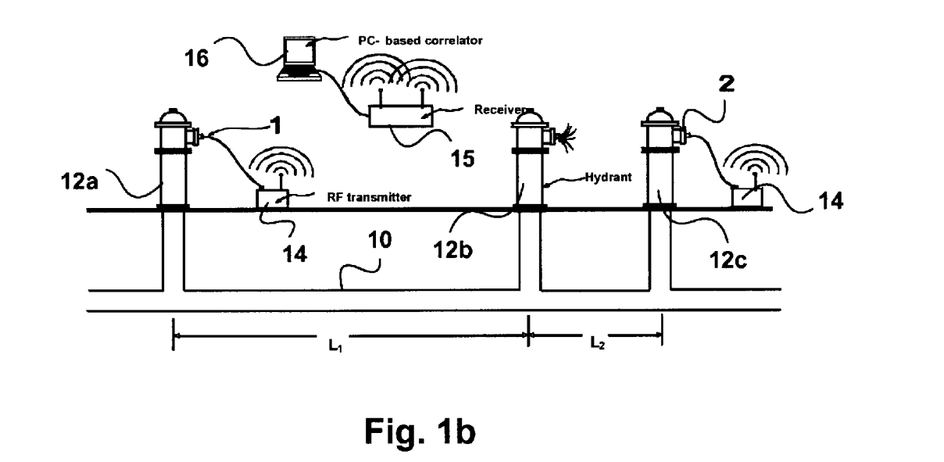
FIG. 1b shows an arrangement for measuring propagation velocity of buried pipes in accordance with a second embodiment.

Typical setups in accordance with embodiments of the invention are shown in FIGS. 1a and 1b. A buried water pipe 10 has hydrants 12a, 12b, 12c. Sensors 1, 2 are mounted on two of the hydrants, while the third provides a source outside the hydrants including the sensors. In FIG. 1a, the sensors are mounted on hydrants 12a and 12b, while the hydrant 12c acts as a source. In this case, the propagation velocity is determined by measuring the propagation time between hydrants 12a and 12b. The propagation velocity is given by the expression v=D/ΔT, where ΔT is the time delay between the signals sensed by sensors 1 and 2, and assuming equal lengths for pipes connecting fire hydrants 12a and 12b to the main pipe 10.

In FIG. 1b, the hydrant 12b acts as the source, and the disturbance is detected by the sensors 1, 2 at hydrants 12a, 12c on either side of the source. In this case, the propagation velocity is given by the expression $v=(L_2-L_1)/\Delta T$, assuming equal lengths for pipes connecting fire hydrants 12a and 12c to the main pipe 10.

Figure 2A:
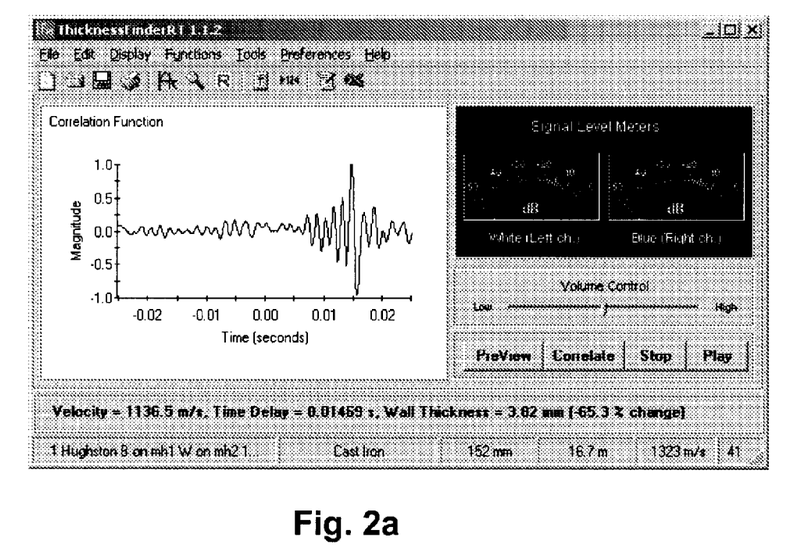
FIGS. 2a and 2b show PC screens displaying the results of a wall thickness measurement in accordance with an embodiment of the invention.
Figure 2B:
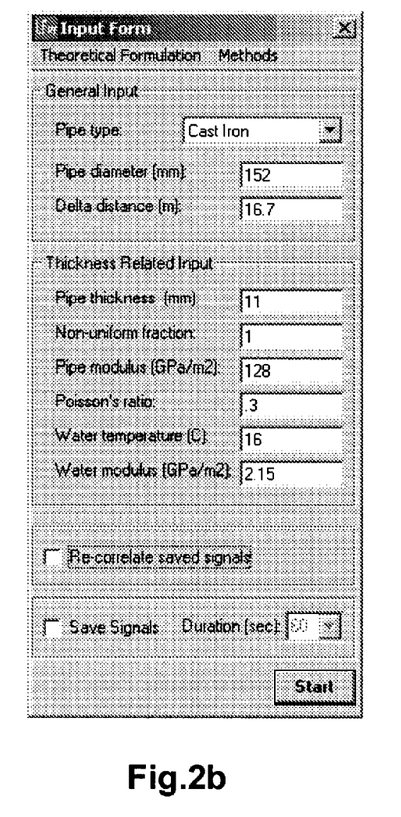

Signals are sent remotely from transmitters 14 attached to the sensors 1, 2 to a receiver 15 connected to PC 16 running a program transferred to its hard drive from a storage medium, such as a CD ROM 18. The computer 16 is Windows™ based (although it will be appreciated that any other suitable operating system can be used) and displays the results in windows shown in FIGS. 2a and 2b. FIG. 2a shows the results of a measurement. FIG. 2b is a screen allowing the user to enter relevant parameters, such as the pipe material, the temperature, etc. The signals may be transmitted in analogue or digital forms. In an alternative setup, signals from the sensors 1, 2 can be sent to the PC via cables. Alternatively, dedicated hardware can be used instead of a PC to calculate the time delay between acoustic signals and determine the pipe's wall thickness.

When sensors are mounted on fire hydrants that are connected to the pipe being tested, the connecting pipes should be traced on the surface and their lengths measured accurately and incorporated in the sensors' distances from the acoustic source. If it is not possible to trace the connecting pipes and hence their lengths are based on a "best guess" of their layout, the lengths should be checked for accuracy. One way of doing so is to measure the propagation velocities of acoustic noise created by at least two sources at different locations. For example, two out-of-bracket sources on opposite sides of the bracket can be used. If distances of the sensors from the acoustic sources are inaccurate due to errors in the lengths of connecting pipes between fire hydrants and the main pipe, the separately measured propagation velocities of acoustic noise induced by the two sources will be different.

A system of linear equations can be formed based on the relationship between time delays of acoustic signals induced by acoustic sources at different locations, acoustic propagation velocity in the pipe, and lengths of connecting pipes. Time delays between measured acoustic noise can be determined using the time-flight method or the cross-correlation function (either traditional or enhanced). The acoustic velocity can then be found by solving the system of linear equations. The number of acoustic sources at different locations should be equal to the number of unknowns. Two or three acoustic sources are sufficient in most cases.

As an example, consider the case in which the sensors 1 and 2 are mounted on fire hydrants that are connected to the main pipe with perpendicular connecting pipes having unknown lengths of $L_1$ and $L_2$, respectively. The distance between the two points where the connecting pipes to the fire hydrants branch out from the main pipe is D and can be measured accurately. The time delays $\Delta t_1$ and $\Delta t_2$ between acoustic signals induced by out-of-bracket sources at the side of sensors 1 and 2, respectively, are related to the acoustic velocity, v, and $L_1$ and $L_2$ by the following equations:

$$\Delta t_1 = \frac{(D + L_2) - L_1}{v} \quad (30)$$

$$\Delta t_2 = \frac{L_2 - (D + L_1)}{v} \quad (31)$$

which can be solved to determine the propagation velocity as follows:

$$v = \frac{-2D}{(\Delta t_2 - \Delta t_1)} \quad (32)$$

The pipe wall thickness determined by the method described represents an average value for the pipe section between the two points where acoustic signals are measured. This is not a limiting aspect of the method. Generally, pipes will have a roughly uniform thickness profile over significant lengths, say 100 metres, as soil and bedding conditions are unlikely to change significantly over wide areas. Even for situations where the longitudinal thickness profile varies, an average thickness profiles is more appropriate and meaningful than discrete thickness values for evaluating the residual life of pipes for the purpose of long-term planning of rehabilitation and replacement needs.

Virtually every water utility in the industrialized countries of the world is facing major challenges in securing capital dollars to replace aging underground water distribution pipes. This non-destructive technology in accordance with embodiments of the present invention to measure pipe metal loss, i.e., to determine the remaining thickness of pipe walls, provides these utilities with a reliable and accurate way to obtain data that allows them to calculate the remaining service life of pipes. This allows the formulation of capital budget plans that are based on technically sound engineering data, which in turn enhances the decision making process.

The invention also has applicability to the oil and gas industry as well as the building industry (e.g., pipes of fire sprinkler systems, which are known to suffer severely from the action of corrosion).

We claim:

1. An apparatus for the non-destructive condition assessment of a pipe carrying a fluid, comprising:
   a) first and second sensors for detecting an acoustic disturbance propagating past two longitudinally separated points on said pipe; and
   b) a processor receiving inputs from said first and second sensors and programmed to:
      (i) determine an actual value representative of the propagation velocity of said acoustic disturbance;
      (ii) compute a corresponding predicted value for the propagation velocity as a function of at least one wall thickness parameter of said pipe by using a theoretical model for the propagation of acoustic waves in said pipe that assumes said pipe has a finite wall thickness with a predetermined circumferential thickness profile; and
      (iii) compute said wall thickness parameter by matching said actual value with said predicted value.

2. An apparatus as claimed in claim 1, wherein said pipe is a water pipe, and said sensors are mounted on support elements selected from the group consisting of: hydrants connected to said pipe, control valves attached to the pipe, and the pipe wall accessed via manholes or small excavated keyholes in the soil.

3. An apparatus as claimed in claim 1, wherein said sensors are inserted into the pipe individually or as arrays thru fire hydrants or corporation stops.

4. An apparatus as claimed in claim 1, wherein said model includes the velocity of propagation of the disturbance in the unbounded fluid or the bulk modulus elasticity of the fluid, the fluid's density, the pipes's internal diameter and wall thickness, and Young's modulus of the material forming the pipe.

5. An apparatus as claimed in claim 1, wherein said sensors are connected to wireless transmitters, and said processor is connected to a receiver for remotely picking up signals from said sensors; or said sensors are connected to said processor via cable.

6. An apparatus as claimed in claim 5, further comprising a reference pipe of known wall thickness profile to permit at least one constant in said theoretical model to be back calculated from actual velocity measurements.

7. An apparatus as claimed in claim 1, wherein said processor is included in a PC or a specially designed device.

8. A storage medium storing coded instructions for instructing a computer to:
   accept signals from sensors responsive to an acoustic disturbance propagating along a pipe;
   compute an actual value representative of the propagation velocity of said acoustic disturbance by dividing the difference between the distances of said sensors from corresponding acoustic source by the time delay between said acoustic disturbances;
   compute a corresponding predicted value for the propagation velocity as a function of at least one wall thickness parameter of said pipe by using a theoretical model for the propagation of acoustic waves in said pipe that assumes said pipe has a finite wall thickness with a predetermined circumferential thickness profile; and compute said wall thickness parameter by matching said actual value with said predicted value.

9. A storage medium as claimed in claim 8, further including instructions for instructing said computer to calculate constants for use in said theoretical model from measurements performed on a reference pipe of known wall thickness.

10. A storage medium as claimed in claim 8, further including instructions to cause said computer to display an input screen for accepting inputs relating to known pipe parameters for use in the computation.

11. A storage medium as claimed in claim 10, wherein said constants include the velocity of propagation of the disturbance in the unbounded fluid and the bulk modulus of the material forming the pipe.

* * * * *